United States Patent [19]

Van Noy et al.

[11] Patent Number: 5,147,393
[45] Date of Patent: Sep. 15, 1992

[54] BIFOCAL INTRAOCULAR LENS WITH CORRECTION FOR SPHERICAL ABBERATION

[75] Inventors: Stephen J. Van Noy, Fort Worth; Anilbhai S. Patel, Arlington, both of Tex.; Thomas Carncross, Kirkland, Wash.

[73] Assignee: Alcon Surgical, Inc., Fort Worth, Tex.

[21] Appl. No.: 681,814

[22] Filed: Apr. 5, 1991

[51] Int. Cl.⁵ ............................................. A61F 2/16
[52] U.S. Cl. ............................................. 623/6
[58] Field of Search ........................ 623/6; 351/161

[56] References Cited

U.S. PATENT DOCUMENTS

| | | | |
|---|---|---|---|
| 4,636,211 | 1/1987 | Nielsen et al. | 623/6 |
| 4,795,462 | 1/1989 | Grendahl | 623/6 |
| 4,813,955 | 3/1989 | Achatz et al. | 623/6 |
| 4,890,913 | 1/1990 | De Carle | 351/161 |

FOREIGN PATENT DOCUMENTS 8902251 3/1989 World Int. Prop. O. .............. 623/6

*Primary Examiner*—Randy C. Shay
*Attorney, Agent, or Firm*—Sally Yeater; James Arno

[57] ABSTRACT

Intraocular lenses with three zones for the provision of bifocal vision are described. Methods for the lenses use are also described.

14 Claims, 1 Drawing Sheet

BIFOCAL INTRAOCULAR LENS WITH CORRECTION FOR SPHERICAL ABBERATION

FIELD OF THE INVENTION

The present invention is directed to artificial intraocular lenses with a bifocal optic.

BACKGROUND OF THE INVENTION

The majority of patients undergoing cataract removal receive an intraocular lens which does not provide for both near and distance vision. These patients then usually require some form of refractive correction, such as spectacles or contact lenses to achieve both near (reading) and distance (driving) vision. There is thus a need for intraocular lenses that will enable cataract surgery patients to perform activities requiring near and distance vision, especially in extreme lighting conditions, without spectacles.

Concentric bifocal intraocular lenses are known. U.S. Pat. No. 4,636,211, issued to Nielsen et. al., discloses an intraocular lens with concentrically oriented near vision and far vision zones, with the near vision portion centrally positioned and the far vision portion coaxial with and surrounding the near vision portion. U.S. Pat. No. 4,813,955, issued to Achatz et. al., discloses a multifocal intraocular lens whose optic portion is divided into near and far range zones such that the rays received by the pupil of the eye pass through near and far range zones of approximately equal areas.

Although prior, concentric, bifocal lenses have optics with portions which will provide for near and distance vision, there can be problems upon implantation due to, among other things, fluctuations in pupil size and spherical aberration phenomenon resulting in non-coincident images from different zones in a lens intended for the same distance correction.

The intraocular lenses of the present invention overcome the aforementioned problems through the use of a three zoned refractive optic for the provision of near and distance vision over the entire pupil range, especially in extreme lighting conditions, with the peripheral distance zone corrected for spherical aberration such that rays of light passing through the central and peripheral zones are coincident in aqueous.

SUMMARY OF THE INVENTION

The lenses of the present invention have an optic portion comprised of three zones. The central zone is for distance vision and is approximately 1.8 millimeters (mm) in diameter. The second annular zone is for near vision, and has an inside diameter of about 1.8 mm and an outside diameter of about 3.0 mm. The second zone also has an increased power over the power for distance vision by 2.5-4.5 diopters in aqueous. The third, or peripheral zone, for distance vision, extends from the outer edge of the second zone to the edge of the optic. Additionally, the radius of curvature of the surface of the peripheral zone has been selected with reference to the central zone to correct for spherical aberration as discussed below.

The lenses of the present invention are used to replace the natural lens of the eye when it is necessary to remove the natural lens, usually due to the development of cataracts.

DETAILED DESCRIPTION OF THE PREFERRED EMBODIMENTS

Figure 1:
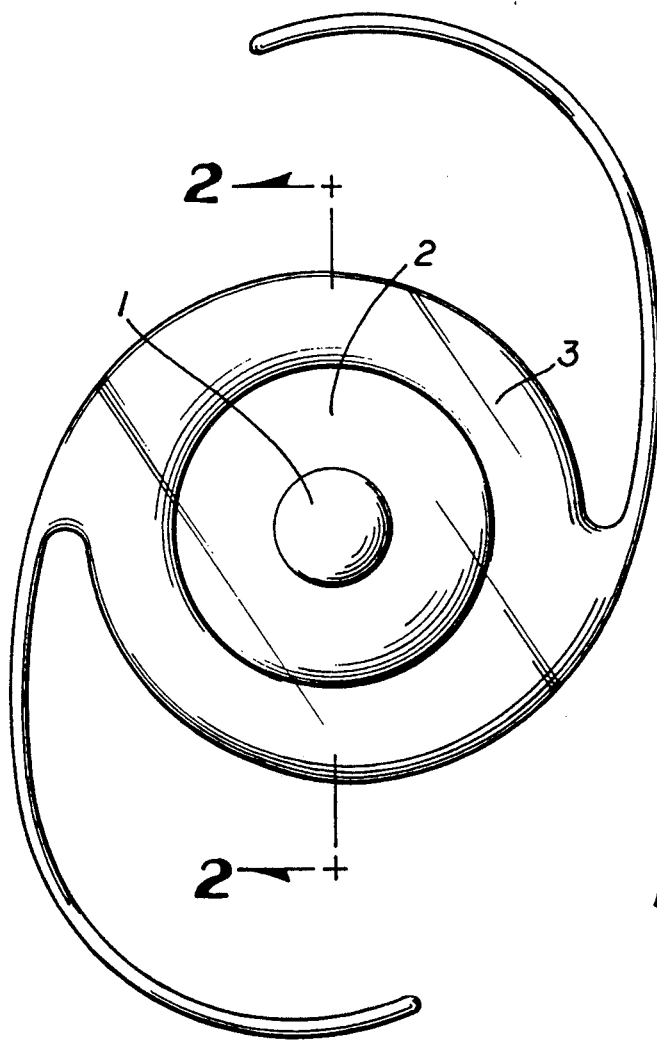
FIG. 1 illustrates the anterior surface of a biconvex, bifocal lens of the present invention.

Intraocular lenses are most frequently implanted in the elderly. Therefore, the lenses of the present invention are designed to best meet the needs of an elderly patient, that is, provide distance vision (greater than 6 meters) throughout the overall pupil range of 1.8-6.5 mm and high resolution near vision (0.35 meters) in a pupil range of 2.5-4.5 mm. To achieve these goals, an intraocular lens with three zones for near and distance vision was created. The intraocular lenses (IOLs) of the present invention can be made of any optically transparent material suitable for an IOL, including, but not limited to, PMMA, soft acrylates (acrylate/methacrylate copolymers), hydrogels, polycarbonates, and silicones. The cross sectional shape of the optic portion of the intraocular lens is not limited, that is, it can be biconvex, plano convex, convex plano, or of a meniscus design. In addition, the optic portion can be of any desired geometry including any geometry, such as oval, such that the lens can be inserted by a surgeon through a relatively small incision in the eye. The lenses of the present invention can include any suitable shape and number of haptics. Any suitable material for use as haptics can be used. Such materials include, but are not limited to, PMMA, polypropylene, and polyimide. In addition, the lenses can be of a single or multi-piece design. Depending on the shape of the optic, the three zones for near and distance vision are placed on either the anterior or posterior face of the optic, the anterior face being that surface of a lens nearest the anterior, or forward, part of the eye and the posterior face, that surface closest to the back or posterior part of the eye. For example, in a biconvex lens, the zones can be placed on either the anterior or posterior surface of the lens. The other surface, not encompassing the zones, can then be manufactured with a single radius of curvature to provide for the additional power so that the total distance and near power of the lens is achieved. The total power of the lens can range from 5 to 39.5 diopters.

The three zones of the intraocular lenses of the present invention have defined sizes to provide for near and distance vision over the entire pupil range. The size of these zones is not dependent on the cross sectional shape of the optic or the materials used in the lens. The central zone, for distance vision, is approximately 1.8 mm in diameter. The second zone is an annulus surrounding the central zone, and has an inside diameter of about 1.8 mm and an outside diameter of about 3.0 mm. The second zone is for the provision of near vision. The third zone, for the provision of distance vision, surrounds the second zone and extends from the outer diameter of the second zone to the edge of the optic.

The radii of curvature of the three zones will vary depending on the type of material used in the optic of the lens. For example, when the optic is made of polymethyl methacrylate (PMMA), a preferred material for the lens of the present invention, the zones have radii of curvature as follows. The central zone's radius of curvature is about 28.54 mm. The second zone's radius of curvature is about 15.70–19.63 mm (this provides for about a 2.5–4.5 diopter increase over the distance vision power). The third zone's radius of curvature is about 30.02 mm. The radius of curvature of the third zone differs from that of the central zone, both of which provide for distance vision, in order to correct for what is referred to in the field as spherical aberration such that rays passing through the central and third zones are coincident in aqueous.

If the radii of curvature of the central and third zones are the same, light which passes through the lens further from the center of the lens, i.e., through the third zone, will focus at a point closer to the anterior or front of the eye in contrast to the rays of light which pass through the lens through the central zone. This phenomenon is known as spherical aberration and prevents the patient from having sharp distance vision over a broad range of pupil sizes which will vary depending upon the amount of light. In order to correct for this effect, the radius of curvature of the third zone of the lenses of the present invention have been adjusted to a value different from that of the central zone so that the rays of light passing through the central zone and the third zone are coincident in aqueous.

Figure 2:
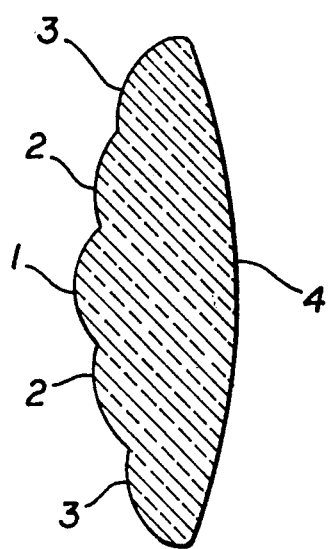
FIG. 2 illustrates a side view of a biconvex, bifocal optic of the present lens invention.

FIGS. 1 and 2 illustrate a preferred embodiment of the present invention. FIG. 1 shows the anterior face of a single piece intraocular lens comprising an optic and two haptics. The anterior face of the optic is comprised of three zones to provide for bifocal vision. The first zone (1) is a central zone for the provision of distance vision. It is about 1.8 millimeters in diameter. The second zone (2) is an annulus with an inside diameter of 1.8 mm and an outside diameter of 3.0 mm for the provision of near vision. The third zone (3) surrounds the second zone and extends from the outer diameter of the second zone to the edge of the optic for the provision of distance vision.

FIG. 2 represents a cross sectional view of the optic of FIG. 1 and shows the radii of curvature of the zones. The central zone (1) has a radius of curvature of about 28.54 mm for the provision of distance vision. The second zone has a radius of curvature of 17.44 mm for the provision of near vision (for about a 3.5 diopter increase over the distance vision power). The third zone (3) has a radius of curvature of about 30.02 mm for provision of distance vision. The radius of curvature for the third zone has been adjusted to correct for spherical aberration making light rays passing through the central and third zones coincident in aqueous. The posterior surface of the optic (4) has a radius of curvature to provide for additional power so that the total distance vision power of the lens is from about 5 to about 35 diopters and the total near vision power is 7.5–39.5 diopters. Within these ranges, the near vision power is greater than the distance vision power by 2.5–4.5 diopters.

The lenses of the present invention can be used to replace the natural lens of the eye by a skilled clinician. The natural lens is most usually removed from the elderly upon their development of cataracts.

The present invention, having been fully described, is only limited as set forth in the following claims.

We claim:

1. A bifocal intraocular lens made of PMMA, having an optic portion comprising a central zone with a radius of curvature of about 28.54 mm, a second zone surrounding said central zone having a radius of curvature of about 15.70 mm–19.63 mm, and a third zone surrounding said second zone having a radius of curvature of about 30.2 mm.

2. A bifocal intraocular lens having an optic portion comprising a central zone comprising means for the provision of distance vision, having a diameter of about 1.8 mm, a second zone comprising means for the provision of near vision, surrounding the central zone, with an inside diameter of about 1.8 mm and an for the provision of distance vision, which extends outside diameter of about 3.0 mm, and a third zone comprising means from the outer diameter of the second zone to the edge of the optic, the radii of curvature of the third zone differing from that of the central zone to correct for spherical aberration such that images formed by the central and third zones are coincident in aqueous.

3. The lens of claim 2 wherein the second zone has a 2.5 –4.5 diopter power increase over the central and third zones.

4. The lens of claim 2 wherein the radius of curvature of the central zone is about 28.54 mm, the radius of curvature of the second zone is about 15.70 mm–19.63 mm, and the radius of curvature of the third zone is about 30.03 mm.

5. The lens of claim 4 wherein the radius of curvature of the second zone is about 17.44 mm.

6. The lens of claim 2 wherein the optic is biconvex.

7. The lens of claim 2 wherein the optic is comprises of a material selected from the group consisting of soft acrylates, hydrogels, silicones, polycarbonates, and PMMA.

8. The lens of claim 7 wherein the topic comprises PMMA.

9. The lens of claim 7 wherein the topic comprises soft acrylates.

10. A method for providing bifocal vision which comprises, selecting an intraocular lens having an optic portion comprising a central zone comprising means for the provision of distance vision, having a diameter of about 1.8 mm, a second zone comprising means for the provision of near vision, surrounding the central zone, with an inside diameter of about 1.8 mm and an outside diameter at about 3.0 mm, and a third zone comprising means for the provision of distance vision, which extends from the outer diameter of the second zone to the edge of the optic, the radii of curvature of the third zone differing from that of the central zone to correct for spherical aberration such that images formed by the central and third zones are coincident in aqueous, and implanting said lens into the eye of a patient.

11. The method of claim 10 wherein said selecting step includes selecting a lens wherein the second zone has a 2.4–4.5 diopter power increase over the central and third zones.

12. The method of claim 10 wherein said selecting step includes selecting a lens wherein the radius of curvature of the central zone is about 28.54 mm, the radius of curvature of the second zone is about 15.70 mm–19.63 mm, and the radius of curvature of the third zone is about 30.02 mm.

13. The method of claim 12 wherein said selecting step includes selecting a lens wherein the radius of curvature of the second zone is about 17.44 mm.

14. The method of claim 12 wherein said selecting step includes selecting a lens wherein the lens is biconvex.

* * * * *

UNITED STATES PATENT AND TRADEMARK OFFICE
CERTIFICATE OF CORRECTION

PATENT NO. : 5,147,393

DATED : September 15, 1992

INVENTOR(S) : Stephen J. Van Noy, et al

It is certified that error appears in the above-identified patent and that said Letters Patent is hereby corrected as shown below:

In Col. 4, lines 9-10,
delete "outside diameter of about 3.0mm, and a third zone comprising means" and insert therefore, -- outside diameter of about 3.0 mm, and a third zone, comprising means --.

Signed and Sealed this

Twenty-first Day of July, 1998

Attest:

BRUCE LEHMAN

Attesting Officer

Commissioner of Patents and Trademarks